United States Patent [19]
Morifuki

[11] Patent Number: 4,883,464
[45] Date of Patent: Nov. 28, 1989

[54] MILKING EQUIPMENT
[75] Inventor: Yaso Morifuki, Osaka, Japan
[73] Assignee: Jex Co., Ltd., Osaka, Japan
[21] Appl. No.: 266,205
[22] Filed: Oct. 27, 1988

Related U.S. Application Data

[63] Continuation of Ser. No. 110,545, Oct. 19, 1987, abandoned, which is a continuation of Ser. No. 783,245, Oct. 2, 1985, abandoned, which is a continuation-in-part of Ser. No. 517,999, Jul. 27, 1983, abandoned.

[30] Foreign Application Priority Data

Aug. 10, 1982 [JP] Japan ................................ 57-138756

[51] Int. Cl.$^4$ .............................................. A61M 1/06
[52] U.S. Cl. .................... 604/74; 119/14.42
[58] Field of Search .................. 604/74, 75, 313, 149, 604/150; 119/14.42, 14.43; 417/411, 413

[56]     References Cited
U.S. PATENT DOCUMENTS

| 897,289 | 9/1908 | Howell | 604/74 |
| 4,323,067 | 4/1982 | Adams | 604/74 |
| 4,397,639 | 8/1983 | Eschweiler | 417/411 |
| 4,759,747 | 7/1988 | Aida et al. | 604/74 |

FOREIGN PATENT DOCUMENTS

| 2658322 | 6/1978 | Fed. Rep. of Germany | 604/74 |
| 3508410 | 9/1985 | Fed. Rep. of Germany | . |
| 2155792 | 10/1985 | United Kingdom | 604/74 |

Primary Examiner—Jerome L. Kruter
Attorney, Agent, or Firm—Koda & Androlia

[57]     ABSTRACT

A milking equipment is formed with an electric suction section, a milk sucking section equipped with an open trumpet at its side, and a bottle connected vertically to each other in a manner to effect vertical communication among them. The electric suction section is equipped with a pressure adjusting screw and a pressure releasing button which can freely adjust the internal pressure by intaking the air. The operation of the pressure adjusting unit is easily attained only by holding the equipment with one hand when the milking is performed, and the back flow of the sucked milk toward the suction section is prevented. The equipment works with easy operation, and the suction force to the mother can be changed readily.

3 Claims, 1 Drawing Sheet

MILKING EQUIPMENT

This is a continuation of application Ser. No. 110,545 filed Oct. 19,1987 now abandoned which is a continuation of Ser. No. 783,245 filed Oct. 02,1985 now abandoned which is a continuation-in-part of Ser. No. 517,949 filed Jul. 27,1983 now abandoned.

BACKGROUND OF THE INVENTION

1. Field of the Invention

The present invention relates to milking equipment, and more particularly to a brest pump for sucking mother's milk.

2. Prior Art

Conventional milking equipment is generally of a filler type or a cylinder type. Recently, it is being considered to change these types of equipment from manual to electrical.

Accordingly, most of today's milking equipment is of the type which feeds the mother's milk into a sucking bottle by a manual suction pump or a cylinder type suction pump. Such milking equipment is defective in that:

1. The suction action is unadjustable;
2. The mother's milk is likely to be forced toward the suction unit;
3. The body is unbalanced and unstable since the suction assembly is provided at the rear part of the trumpet which sucks the mother's milk; and
4. It requires both hands for sucking the mother's milk.

On the other hand, an electric milking equipment which has been recently placed on the market has potential problems. It is not easy to handle due to the complex structure in which the electric suction device is connected to the main unit separately from the milk sucking section. It is also not easy to adjust it with one hand. Furthermore, all such devices have a suction action which is unified and causes the mother's milk to be sucked one-sidedly so that the breast has to increase its burden upon the mother, who inevitably feels displeasure.

In the meantime, the U.S. Pat. Nos. 4,249,481 and 4,263,912 disclose an improved milking apparatus and method. The apparatus is designed so as to apply suction at least to a nipple synchronously as well as selectively or in either manner when a manual fastening force is exerted to both or either of the nipples and the breast. Accordingly, it requires manual acting force, is difficult to use with one hand, and has difficulty in operation and in suction pressure adjustment.

SUMMARY OF THE INVENTION

The purpose of the present invention, created in light of the foregoing problems, is to provide milking equipment for mother's milk in which a pressure adjusting screw for adjusting the internal pressure in a milk sucking section and a pressure releasing button are mounted on an electric suction assembly. The suction assembly and the sucking section with a trumpet at its side and a storing bottle are vertically connected to communicate with each other so as to operate the pressure adjusting device easily only with one hand. The effect produced by such a simple structure is identical to the process in which the breast is squeezed by hand with easy operation for the main unit. The equipment of the invention can achieve high milking capacity with manual pressure adjustment for sucking.

BRIEF DESCRIPTION OF THE DRAWINGS

The accompanying drawings illustrate the preferred embodiment of the milking equipment according to the present invention, and in which.

DETAILED DESCRIPTION OF THE INVENTION

Figure 1:
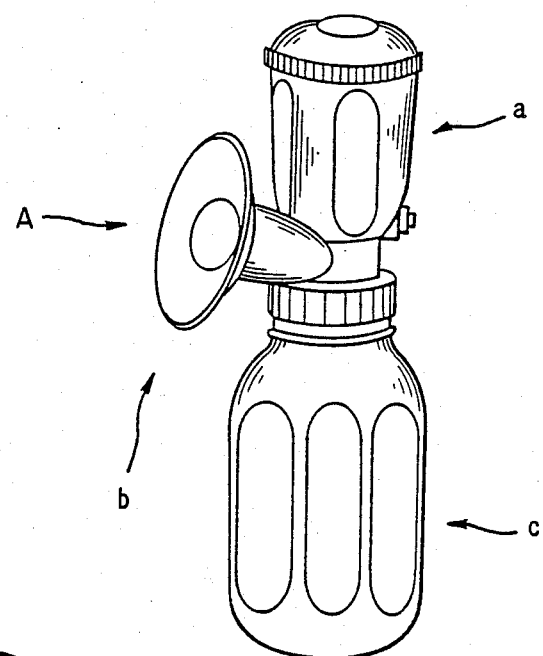
FIG. 1 is a perspective view of the milking equipment of this invention.

FIG. 1 is a perspective view illustrating the milking equipment according to the present invention. The milking equipment A includes a suction assembly a, a milk sucking section b equipped with an open trumpet at its side and a bottle c which are vertically connected to communicate with each other.

Figure 2:
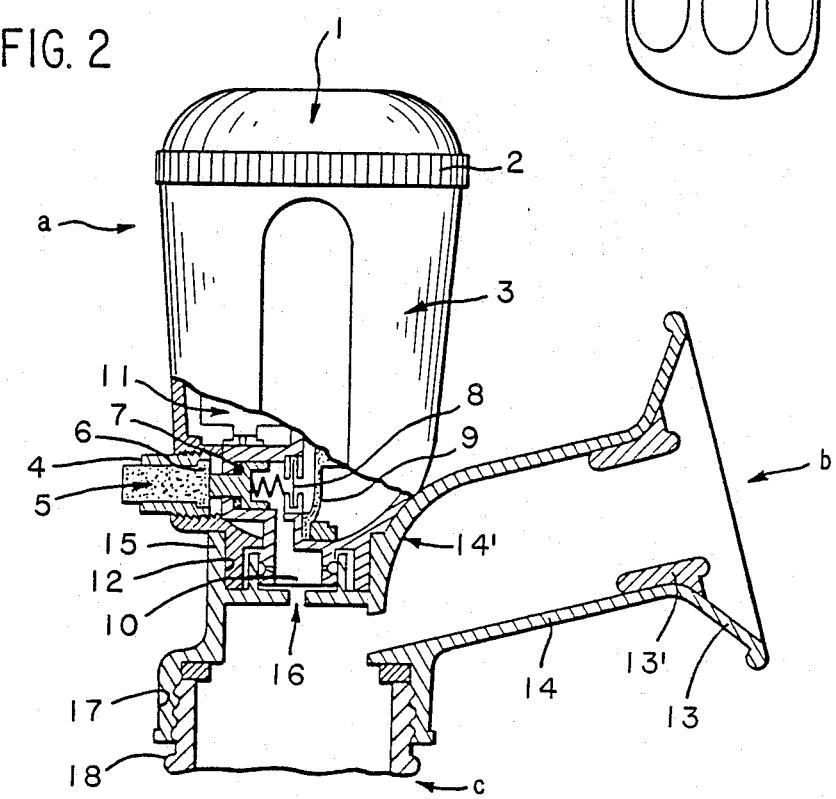
FIG. 2 is a partially cut-away enlarged sectional view illustrating the suction assembly, milk sucking section and a bottle.

FIG. 2 is a partially cut-away enlarged sectional view illustrating the structure in which the suction assembly a, the milk sucking section b, and the bottle c are connected and communicated with each other.

Referring now to FIG. 2, an upper lid 1 having a switch 2 and a lower main body 3 form the suction assembly a. The upper lid 1 and a cover of the main body 3 are adapted to employ a rotational structure so that the switch 2 is a sliding type mechanism. The internal structure of the main body 3 is arranged such that at the lower part of the body 3, or at the section connected to the milk sucking section b, a pressure adjusting screw 4, a pressure releasing button 5, a pressure shaft 6, an O-ring 7, a suction valve 8 and a diaphragm 9 are arranged in a successive manner and an air suction inlet 10 is provided beneath the suction valve 8 so as to communication with the valve 8, as shown in FIG. 2. The pressure adjusting screw 4, a means for adjusting the suction pressure, is screwed into the side of the suction assembly a. The pressure releasing button 5 is held inside the pressure adjusting screw 4 such that the button 5 does not move toward the outside. The pressure releasing button 5 pushes the pressure shaft 6 by itself or in cooperation with the pressure adjusting screw 4. When the pressure adjusting screw is turned, the button 5 moves together with the pressure adjusting screw 4 to vary the amount of intake air to the main body in accordance with the size of the space between the O-ring 7 and the wall of the space wherein the O-ring 7 is provided. The numeral 11 is a battery. With this arrangement, if the switch 2 is turned on, an electric mechanism (not shown) causes the diaphragm 9 to vibrate, and suction of the air from the air suction inlet 10 occurs by way of the suction valve 8. In particular, when the diaphragm 9 vibrates to the left in FIG. 2, the valve 8 pushed to the left by the inner pressure inside the diaphragm section, closing the valve 8 and venting the air to the outside via the exhaust valve (not shown). When the diaphragm 9 vibrates to the right, the valve 8 moves to the right by the negative pressure in the diaphragm section, opening the valve 8 while maintaining an exhaust valve in a closed state. As a result, a negative pressure is generated at the air suction inlet 10 which is connected to valve 8 and sucks the air from the bottle c. Furthermore, since the top of the bottle c and the root of the drum 14 of the trumpet 13 communicate with the hole 16 provided between the air suction inlet 10, the air in the drum 14 of the trumpet 13 is sucked into the air suction inlet 10 through the hole 16 together with the air in the bottle c when a negative pressure is formed in the air suction inlet 10. As a result, the inside of the bottle c is provided with a negative pressure.

The sucking assembly b includes a trumpet 13 opening at the side of the assembly b, a drum 14, an upper junction part 15, and a lower junction part 17. The inside of the trumpet 13 is equipped with an adaptor 13' so that the trumpet 13 touches a mastitis of the nipple as close as possible. The top portion of the inside of the drum 14 is curved, and a guide wall 14' is provided along the upper junction part 15. The guide wall 14' is designed to project downward by forming its length slightly longer than the upper junction part 15. Furthermore, the upper junction part 15 is secured to a fitting part 12 formed at the bottom of the main body 3, communicating with a hole 16 provided under the air suction inlet 10. The outer edges of a mouth 18 is of the bottle c is covered with the lower junction part 17 so that the bottle c and the milk sucking section b communicate with each other.

A description of the manner to use the milking equipment of this invention in which the suction assembly a, the milk sucking section b and the bottle c vertically communicate with each other and its acting effect will be shown below.

When the switch 2 is turned on upon completion of putting the nipple into the trumpet 13, the suction assembly a works so that the inside of the bottle c is provided with negative pressure, whereby the milk starts being sucked. The mother's milk is sucked into the inside of the trumpet 13, flowing along the drum 14 and the guide wall 14', and sent into the inside of the bottle c to be collected. At this time, if the pressure adjusting screw 4 is turned, and the pressure shaft 6 is pressurized to move so that the space in which the O-ring is inserted is enlarged, the air flows into the space so that the pressure in the inside of the bottle c communicating with the air suction inlet 10 is decreased. As a result, the milking force and the suction are decreased, and the inside of the bottle c become still. In that case, the adjusting capacity ranging from full opening (or releasing) to complete closing is controlled by the amount of turning of the pressure adjusting screw 4, so that the magnitude of the milking force may be changeable. In addition to this, when the pressure releasing button is depressed, similarly to the foregoing case of the pressure adjusting screw 4, the pressure shaft 6 is forced down at once so that the space in the part in which the O-ring 7 is inserted is enlarged, and a great amount of air flows into to make the pressure in the bottle c communicating to the outside normal.

As will be understood from the foregoing description, the effect produced by the present milking equipment is that it can provide changeable suction force which the breast pumps on the market are unable to. That is, the equipment can provide suction force under certain conditions, and the pressure adjustment and pressure releasing can be made so that the decrease of pressure from a certain level may be attained. Namely, with the intermittent use of the pressure adjusting screw 4 and pressure releasing button 5, the nipple is given an adequate stimulus so that a massage effect is also produced around it. Consequently the milking effect is quite identical to that obtained by squeezing the nipple.

Next, due to the arrangement in which the suction assembly a, milk sucking section b and the bottle c are vertically connected to communicate with each other, and the guide wall 14' of the trumpet 13 is projected downwardly, the present milking equipment can prevent the mother's milk from flowing back into the case of the main body 3. That is, the present invention overcomes such a shortcoming of the conventional breast pump that the mother's milk is likely to be sucked into the suction device.

The present milking equipment is in a stable shape to avoid overturning by providing the suction assembly a on the upper side and has overcome the problem in the conventional breast pump which has at the rear part of the trumpet (milk sucking section) the device for suction that causes a weight imbalance and difficulty in self-standing.

The milking equipment makes it easy to perform milking with only one hand unlike a filler type pump and cylinder type pump which require both hands to operate. Therefore, the other hand can assist the milking by giving a rubbing-massage to the breast.

Thus, the milking equipment according to the present invention is formed vertically in a simple structure which is easy to operate, can milk by easy operation to the pressure adjusting device with one hand and in inexpensive to manufacture while considering the safety and health of a nursing mother.

I claim:

1. A milking equipment comprising a suction assembly, a milk sucking section, and a bottle, said equipment is characterized in that a suction pressure adjusting screw and a pressure releasing button which works in cooperation with said pressure adjusting screw, are provided on the outside of the case of an electric type suction assembly, which includes batteries, such that the amount of air taken into an outer air intake portion through said pressure releasing button and a pressure shaft can be adjusted by turning said pressure adjusting screw, and an air sucking valve of the electric type suction assembly communicates with the outer air intake portion and an air intake which is provided at the lower portion of the suction member, and said suction assembly milk sucking section equipped with an open trumpet at its side, and said bottle are connected vertically to communicate with each other.

2. A milking equipment according to claim 1, wherein a guide wall preventing the milk from flowing ack is provided in a body of a trumpet which is secured to said milk sucking section.

3. A milking equipment according to claim 1 or 2, wherein a detachable adaptor for fitting closely a trumpet to a nipple is provided in said trumpet secure to said milk sucking section.

* * * * *

UNITED STATES PATENT AND TRADEMARK OFFICE
CERTIFICATE OF CORRECTION

PATENT NO. : 4,883,464

DATED : November 28, 1989

INVENTOR(S) : Yasuo Morifuji

It is certified that error appears in the above-identified patent and that said Letters Patent is hereby corrected as shown below:    On the title page Column [75] Inventor:  Change "Yaso Morifuki, Osaka, Japan" to --Yasuo Morifuji, Osaka, Japan--

Signed and Sealed this

Ninth Day of October, 1990

Attest:

HARRY F. MANBECK, JR.

Attesting Officer

Commissioner of Patents and Trademarks